(12) United States Patent
Pryme (10) Patent No.: US 7,550,159 B2
(45) Date of Patent: Jun. 23, 2009

(54) ORALLY INGESTIBLE PREPARATION OF MISTLETOE LECTINS AND METHOD

(75) Inventor: Ian Pryme, Bergen (NO)

(73) Assignee: Palm Research AS, Bergen (NO)

( * ) Notice: Subject to any disclaimer, the term of this patent is extended or adjusted under 35 U.S.C. 154(b) by 71 days.

(21) Appl. No.: 10/416,463

(22) PCT Filed: Nov. 12, 2001

(86) PCT No.: PCT/NO01/00446

§ 371 (c)(1),
(2), (4) Date: Sep. 22, 2003

(87) PCT Pub. No.: WO02/40041

PCT Pub. Date: May 23, 2002

(65) Prior Publication Data

US 2004/0052869 A1    Mar. 18, 2004

(51) Int. Cl.
*A61K 36/00* (2006.01)
*C07K 14/42* (2006.01)

(52) U.S. Cl. .................. 424/725; 530/396; 530/395; 530/370

(58) Field of Classification Search .............. None
See application file for complete search history.

(56) References Cited

U.S. PATENT DOCUMENTS 5,595,756 A * 1/1997 Bally et al. ............ 424/450

FOREIGN PATENT DOCUMENTS

DE    4229876    *   3/1994
DE    4421895 A   *   1/1996

OTHER PUBLICATIONS

Eifler, R. et al. Improved Procedures for Isolation of Mistletoe Lectins and Their Subunits: Lectin Pattern of the European Mistletoe; Lectins: Biochemcistry and Clinical Biochemistry, vol. 9, (1993) pp. 144-151.*

Franz, M et al. Isolation and Quantification of Chitin-Binding Mistletoe Lectin From Mistletoe Extracts and Validation of This Method; Arzneimittelforschung, 2004; 54(4), pp. 230-239.*

Kopp, J. et al. Toxicity of Mistletoe Lectins I, II , III on Normal and Malignant Cells; Lectins: Biology, Biochemistry, Clinical Biochemistr; vol. 8, (1993), pp. 41-47.*

Wacker, R. et al. Complete Structure Determination of the A Chain of Mistletoe Lectin III From Viscum Album L. SSP. Album; J. Peptide Science Mar. 2004, 10 (3): 138-48.*

(Continued)

*Primary Examiner*—Patricia Leith
(74) *Attorney, Agent, or Firm*—Christian Abel (57) ABSTRACT

An orally ingestible preparation consisting essentially of Mistletoe lectin I (ML-I), Mistletoe lectin II (ML-II), and Mistletoe lectin III (ML-III), which specifically excludes the nausea-inducing compounds present in mistletoe extracts. The invention also provides for a method of producing said preparation, a method of using said preparation to produce pharmaceutical preparations, and a method for using said preparation in the treatment of patients suffering from cancer and auto immune diseases.

6 Claims, 3 Drawing Sheets

OTHER PUBLICATIONS

Gura, T. Systems for Identifying New Drugs are Often Faulty; Science, vol. 278, Nov. 1997, pp. 1041-1042.*

Zarkovic, et. al., "Comparison of the effects of Viscum album LEctin ML-I and Fresh Plant Extract (Isorel) on the Cell Growth in vitro and Tumorigenicity of Melanoma B16F10", Cancer Biotherapy, V. 13, n. 2, p. 121 (1998).

Pryme et al, "The induction of gut hyperplasia by phytohaemagglutin in the diet and limitation of tumor growth", Histology Histopathology (1998) 13:575-583 et al.

Pryme et al, "Mistletoe lectin supplementation and reduced growth of a murine non-Hodgkin lymphoma", Histology Histopathology (2002) 17:261-271.

Pryme et al, "A mistletoe lectin (ML-I)-containing diet reduces the viability of a murine non-Hodgkin lymphoma tumor", Cancer Detection and Prevention, 28 (2004) 52-56.

Pryme et al, "Suppression of growth of tumor cell lines in vitro and tumours in vivo by mistletoe lectins", Histology and Histopathology, (2006) 21:285-299.

Nielsen & Nawaz, "Mistletoe lectins in cancer thereapy", Dissertation submitted to the Medical Faculty, Universsty of Bergen, Norway, Autumn 2002.

Winge et al, "A mistletoe tea containing lectins taken orally by humans provokes an immune response and induces an increase in the population of natural killer cells", Submitted for publication (2007).

Hall, et al, "Assessing Mistleto Toxicity", Annals of Emergency Medicine, Nov. 15, 1986.

Krenzelck et al, "American Mistletoe Exposures" American Journal of Emergency Medicine, Sep. 15, 1997.

Kaegi, "Unconventional Therapies for cancer: 3 Iscador" Canadian Medical Association, 5:5(158) 1998.

Stein, GM et al., "Viscotoxin-Free Aqueous Extracts from European Mistletoe (*Viscum album* L.) Stimulate Activity of Human Granulocytes", AntiCancer Research, pp. 2925-2928; 19 (1999).

* cited by examiner

I and II : two separate preparations of mistletoe lectins showing presence of individual protein subunits.

FIGURE 3.

Molecular weight
standards
(kDa)

I  II 97.4

66

45

29 ← ← Mistletoe lectin subunits

I = serum from a person (control) who had not taken PALM.

II = serum from a person who had ingested PALM
for > 6 months, showing positive reaction for presence
of antibodies against mistletoe lectin subunits.

ORALLY INGESTIBLE PREPARATION OF MISTLETOE LECTINS AND METHOD

TECHNICAL FIELD

The present invention relates to medicinally useful preparations derived from mistletoe, methods for making such preparations and treatment methods employing such preparations. More specifically, the invention relates to an orally ingestible preparation of mistletoe lectins useful in the treatment of cancer and other diseases.

BACKGROUND ART

Lectins and Immunomodulation

The cytotoxic cells of the immune system, cytolytic T cells (CTL), natural killer (NK) cells and macrophages, can seek out and ultimately lyse tumor cells either spontaneously or more often after appropriate activation. Spontaneous cytotoxic activity against tumor cells is mainly a result of NK cells. Various cytokines, alone or in combination, have been shown to augment anti-tumor activity : IL-2, IL-7, IL-12 and IFN-γ induce cytotoxic activity in NK and T-cells while IFN-γ and TNFα are potent activators of macrophages and monocytes. Most of the studies that have demonstrated these effects have been confined to in vitro systems although recently the anti-tumor effect of some of these cytokines has also been demonstrated in vivo in animals and also in humans. Lymphocytes cultured in the presence of high amounts of IL-2 are refered to as lymfokine-activated killer (LAK) cells. LAK cells are characterised by their ability to kill NK-resistant tumor cells without major histocompatibility complex (MHC) restriction. Although both NK and T cells are responsible for LAK activity, the former are responsible for mediating most of the activity. Macrophages and monocytes are known to accumulate around tumors. Following the TNFα and IFN-γ stimulated activation of these cells it is predicted that a local release of cytokines would occur from these activated cells directly into the tumor. This in turn would be expected to induce apoptosis and ultimately cause death of the tumor cells.

Besides cytokines, a variety of natural or synthetically produced protein mixtures have been reported to exert immunomodulating properties. The commercially available mistletoe extracts belong to this category of agents. Biochemical analysis has shown that the immunomodulating capacity is due to the presence of mistletoe lectins (ML-I, ML-II and ML-III) in the extracts.

Mistletoe Extracts and Use in Cancer Therapy.

Mistletoe extracts have been used in cancer therapy for more than 80 years, particularly in clinics in Austria, Switzerland and Germany. Use of these extracts has been heavily criticized by practitioners of traditional "school medicine" due to the lack of knowledge concerning the actual nature of active anti-cancer components in mistletoe. Recent work has now clearly shown that purified lectins (ML-I, ML-II, ML-III) present in mistletoe extracts possess both immunomodulatory and cytotoxic properties. The arguments which have been raised by advocates of "school medicine" are thus to a large extent no longer valid.

Treatment methods employing known mistletoe extracts have several disadvantages, however. In the first place, commercially available extracts vary greatly in terms of their composition, thus making both study and treatment regimes unreliable. Furthermore, it is generally believed that mistletoe is toxic. The most common method of clinically treating cancer patients with mistletoe extracts, therefore, has been through subcutaneous injection. Recent work, however, has shown that serum glycoproteins effectively bind to and thus will minimise the effects of mistletoe lectins injected into cancer patients. This suggests that the subcutaneous route is probably not very effective. An alternate delivery method is therefore desirable.

Dietary Lectins and Tumor Growth

As has been shown in a series of publications since 1994 (see references), the growth of intraperitoneal or subcutaneous non-Hodgkin lymphoma tumors in NMRI mice can be reduced by feeding the animals a diet containing the lectin present in raw kidney bean (*Phaseolus vulgaris*), phytohaemagglutinin (PHA) or mistletoe lectin (ML-I). Other observations have shown that the development of a subcutaneous plasmacytoma tumor (MPC-11) in Balb/c mice can be greatly reduced by feeding a diet that included PHA. The lectins, being resistant to the proteolytic effect of gut enzymes, retain their biological activity in the alimentary canal. When added to the diet of experimental animals they bind to the surface of the gut mucosa and induce a fully reversible, dose-dependent hyperplastic growth of the small intestine. Simultaneously with the stimulated gut growth PHA induces an extensive absorption of amino acids and other nutrients from the intestinal lumen. Prior to the onset of hyperplastic growth, an extensive accumulation of extracellular polyamines occurs in the intestinal mucosa. Polyamines are molecules which play major roles in a series of important mechanisms controlling cell proliferation and, importantly, are involved in tumor growth.

In experiments to study the importance of the timing of feeding mice the PHA-containing diet with respect to when the tumor cells were injected, diets were changed on specific days. It was shown that the number of tumor cells was significantly lower when the lactalbumin-based (La) diet was replaced by one supplemented with PHA on the same day as tumor cells were injected. Recent experiments have shown that when PHA was added to the diet of mice bearing established NHL tumors then further growth was greatly retarded. Preliminary data have shown that PHA fed to rats causes a rapid increase in TNFα production. Accelerated cellular turnover within the transplanted NHL tumor as a response to oral intake of ML-1 was seen as increased numbers of apoptotic cells with an increased area of serpiginous irregular dead cells, and the non-viable cells occupied a two fold increased area in the mice fed the lectin. Apoptoses were more numerous in the tumors of mice fed ML-I and these were identified by nick end-labelling around areas of non-viable tumor cells, at the advancing edge of the tumor and within intense lymphoid aggregates. Morphological studies of tumor sections showed a greatly reduced incidence of tumor vascularisation indicating that ML-1 induces the production of anti-angiogenic factors. Recent experiments performed with purified ML-III have shown that feeding of the lectin to mice bearing established NHL tumors was extremely effective in reducing further tumor growth.

While it has thus been shown in animal models that the purified mistletoe lectins are well tolerated when administered orally, the purified mistletoe lectins are extremely expensive and time consuming to produce, making them less than ideal candidates as a treatment method. There is a need, therefore, for a preparation of mistletoe lectins and related treatment method that can be administered orally and that is inexpensive to produce.

Although it is generally believed that mistletoe is toxic, a recent study concerning the outcome of 1754 exposures has shown that accidental ingestion of the plant is not associated with profound toxicity. There are, however, components present in mistletoe extracts that do induce nausea. These nausea-inducing compounds, including alkaloids and viscotoxins, have been mistakenly regarded as essential to the medicinal effectiveness of mistletoe extracts. (See, for example, U.S. Pat. Nos. 5,637,563 and 5,547,674). As a result, no effort has been previously undertaken to produce a mistletoe preparation that can be satisfactorily administered orally to humans.

A procedure for producing purified mistletoe lectins is described by R. Eifler, K. Pfüller, W. Göckeritz and U. Pfüller in "Lectins : Biology, Biochemistry and Clinical Biochemistry" vol. 9 (1993) pp 141-151, which is incorporated by reference herein.

The applicant has recognized that the complex procedure used by Eifler et al to isolate and purify the three individual mistletoe lectins (ML-I, II and III) is not suitable for producing a therapeutic, orally ingestible lectin preparation, however. The rationale being:

(i) The applicant has shown that ML-1, when added to the diets of mice on the same day as tumor cell injection, reduces the mass of non-Hodgkin lymphoma tumors related to controls. A clear dose-response was observed. At the highest amount of ML-1 ingested a total ablation of tumors was seen in 25% of animals. Furthermore, the applicant has recently shown that when purified ML-III was fed in the diet to mice 5 days after subcutaneous injection of Krebs II cells (non-Hodgkin lymphoma), then the growth of the established tumor was arrested. Since the three lectins have different biological specificities (e.g. sugar binding) then they may well act better in concert than if supplied separately. Purifying the individual lectins is therefore counterproductive from a medicinal point of view.

(ii) the complete purification procedure for the three lectins is considerably time consuming, and (iii) the lectin preparation according to the invention showed surprisingly, and contrary to the accepted belief in the art, that it could be taken orally. Thus a small contamination by other proteins would not represent any major problem since proteins other than the lectins would be subject to breakdown by digestive enzymes.

The applicant has therefore modified and improved upon the procedure of Eifler et al. in order to arrive at a mistletoe lectin preparation that contains the lectins ML-I, ML-II and ML-III, possibly together with insignificant amounts of impurities, but which specifically excludes the nausea-inducing compounds otherwise present.

DISCLOSURE OF THE INVENTION

Objects and Advantages of the Invention

The obvious advantage of providing mistletoe lectins by the oral route is that large amounts of the lectins, through their binding to the gut mucosa followed by endocytosis, are in due course presented to lymphocytes of Peyers patches and thereby able to induce a major cytokine response. As has been observed, a major reduction in the weight of the spleen occurs following feeding PHA to mice. This can be attributed to a major release of lymphocytes into the blood circulation as a result of cytokine release from lymphocytes of Peyers patches. It is highly unlikely that such a response would be evoked by the small amounts of lectins that are able to reach the lymphatic tissue when mistletoe extracts are injected subcutaneously. Furthermore, seen from the patients point of view, it is obvious that taking the preparation of mistletoe lectins by the oral route is far more acceptable, and convenient, than by injection.

Based on observations from an animal model system, unpublished work and published data, the following immunomodulating effects are proposed following the oral intake of the mistletoe lectin preparation according to the invention:

1. ML's bind strongly to the gut mucosa.
2. ML's are effectively endocytosed through the mucosa of the small intestine.
3. Binding of endocytosed ML's to lymphocytes of Peyers patches.
4. Stimulation of cytokine release and activation of NK cells etc.
5. Production and release of anti-angiogenic factors.
6. Cytotoxic effects on tumor cells.
7. Reduced tumor vascularisation.
8. Induction of apoptosis leading to tumor cell death.

In addition to the immunomodulating effects from oral intake, the mistletoe lectin preparation also provides a direct cytotoxic effect on tumors with which it comes into direct contact. The individual mistletoe lectins of the preparation are comprised of two chains, A and B. The B chain binds to receptors on the surface of tumor cells, causing endocytosis of the A chain (internalization of the A chain into the tumor cell). The A chain exhibits N-glycosidase activity which results in specific degradation of ribosomal 28S RNA, further resulting in inhibition of protein synthesis leading to tumor cell death.

SUMMARY OF THE INVENTION

Preparation of Mistletoe Lectins and Process

According to the present invention, the nausea-inducing compounds are removed from a mistletoe extract by cationic exchange column chromatography, thus producing a preparation consisting essentially of lectins ML-I, ML-II and ML-III. The preparation may contain insignificant amounts of other, non-nausea inducing components without reducing the biological/medicinal effectiveness of the preparation.

Secondary Medical Indications and Method of Use

According to the present invention, the mistletoe lectin preparation may be administered as a raw chemical composition, or it can be used to produce a nutritional supplement and/or a pharmaceutical preparation that may be administered in therapeutically effective doses for the treatment of cancers as well as autoimmune diseases, such as arthritis, rheumatic diseases, asthma and emphysema, and subjects suffering from general fatigue. Such doses may be in a form suitable for oral, rectal, nasal, topical, vaginal or aerosol administration, or in a form suitable for inhalation or bladder infusion.

Use in Conjunction with Arginine

As discussed in the examples, the applicant has discovered that the effectiveness of the mistletoe lectin preparation is enhanced when the preparation is administered together with a regimen of oral arginine. L-arginine can generally be described as a NO donor. It has been observed that arginine increases endothelium function in tumors, whereby the vessel walls in the tumor tighten up and are not as easily permeable to glucose and proteins. This in turn decreases the nutritional situation for the tumor, which supplements a similar mechanism and effect of the mistletoe lectin preparation. Arginine has also been observed to have a stimulating effect on the immune system, again complimenting a similar effect of the mistletoe lectin preparation.

DETAILED DESCRIPTION OF THE INVENTION

Preparation and Method.

Figure 1:
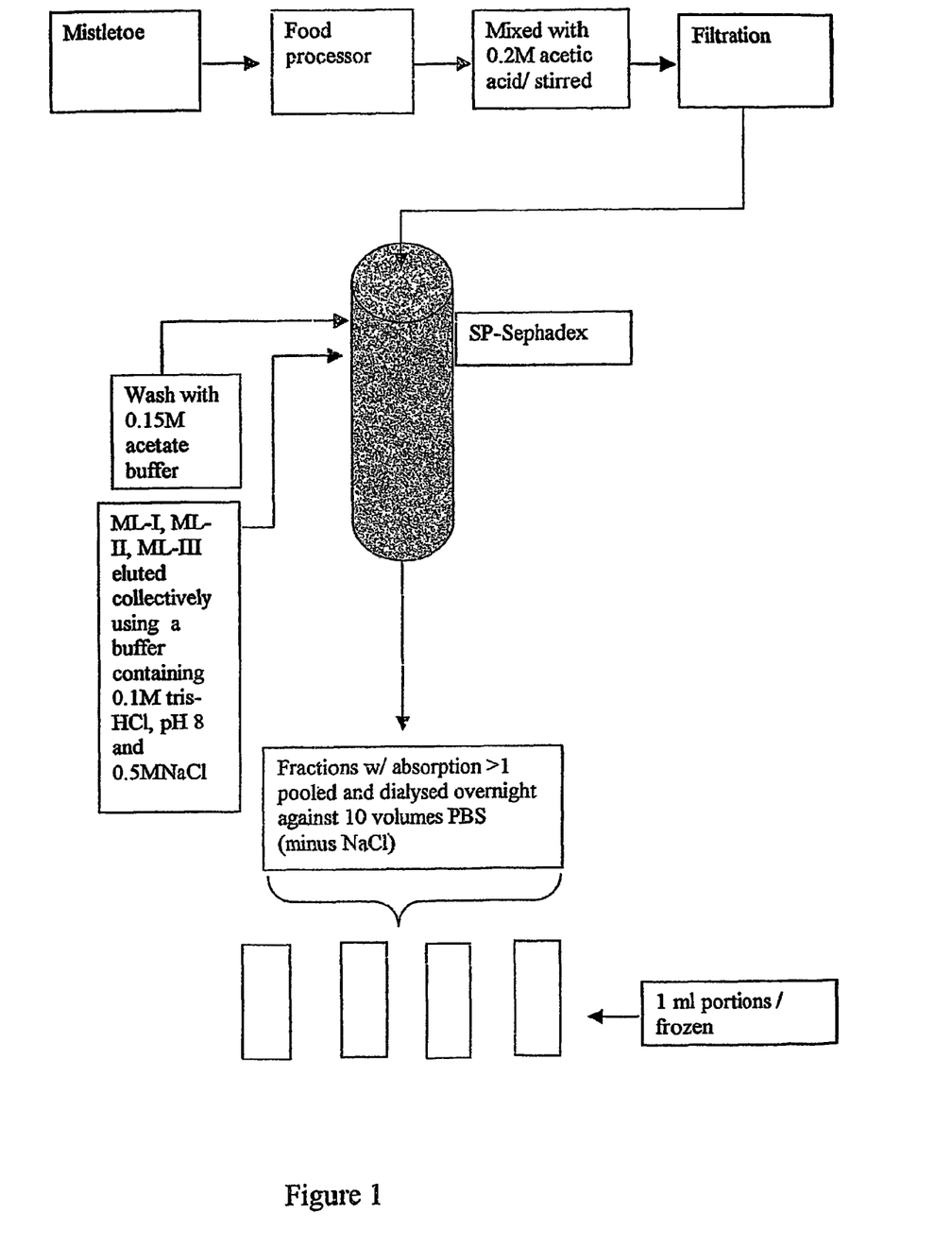
FIG. 1 is a schematic representation of the method of producing the mistletoe lectin preparation according to the invention.

Referring to FIG. 1, the following method is used to produce the mistletoe lectin preparation:

Source of mistletoe: *Visci Alba Herba* 4 mm from Norsk Medisinaldepot (or *Viscum album* generally).
1. Mistletoe pulverized using a food processor.
2. Material mixed with 0.2M acetic acid (five times amount on a w/w basis). Stirred overnight at 4° C.
3. Rough plant remains removed by filtration through a coarse cloth followed by filtration through a 240 mm paper filter to remove turbidity.
4. Cationic exchange chromatography performed using approximately 5 g SP-Sephadex cation exchanger/1.0 litre of crude mistletoe extract.
5. Column washed with 0.15M acetate buffer (pH 4.0) until absorption at 280 nm<0.05. This step removes components which do not have the capability of binding to the cationic exchanger.
6. ML-I, II and III lectins eluted collectively using a buffer containing 0.1M Tris-HCl, pH 8.0, and 0.5M NaCl.
7. Fractions with absorption at 280 nm>1.0 pooled and dialysed overnight (4° C.) against 10 volumes of PBS (minus NaCl). The dialysis membrane has a cutoff size of MW 10,000 in order to remove molecules of low MW.
8. The preparation is aliquoted in 1 ml portions and frozen at −20° C. for storage purposes.

The procedure according to the invention differs from that of Eifler et al in several ways:
a) the period of stirring with acetic acid was extended in order to achieve maximal extraction of lectins.
b) filtration through a filter paper following the intial use of coarse cloth was found important to produce a turbid-free extract.
c) the paper filtered acetic acid extract was pumped on to the column rather than being pre-mixed with the cationic exchanger. This was found to be more convenient, especially when handling large volumes.
d) in order to achieve a concentrated, medicinally effective preparation of mistletoe lectins, only those fractions where absorbance at 280 nm was high (>1.0) were chosen to collect and pool.
e) the pooled fractions were dialysed against salt-free buffer in order to remove low MW components and to reduce the NaCl concentration since the preparation was to be taken orally.

Figure 2:
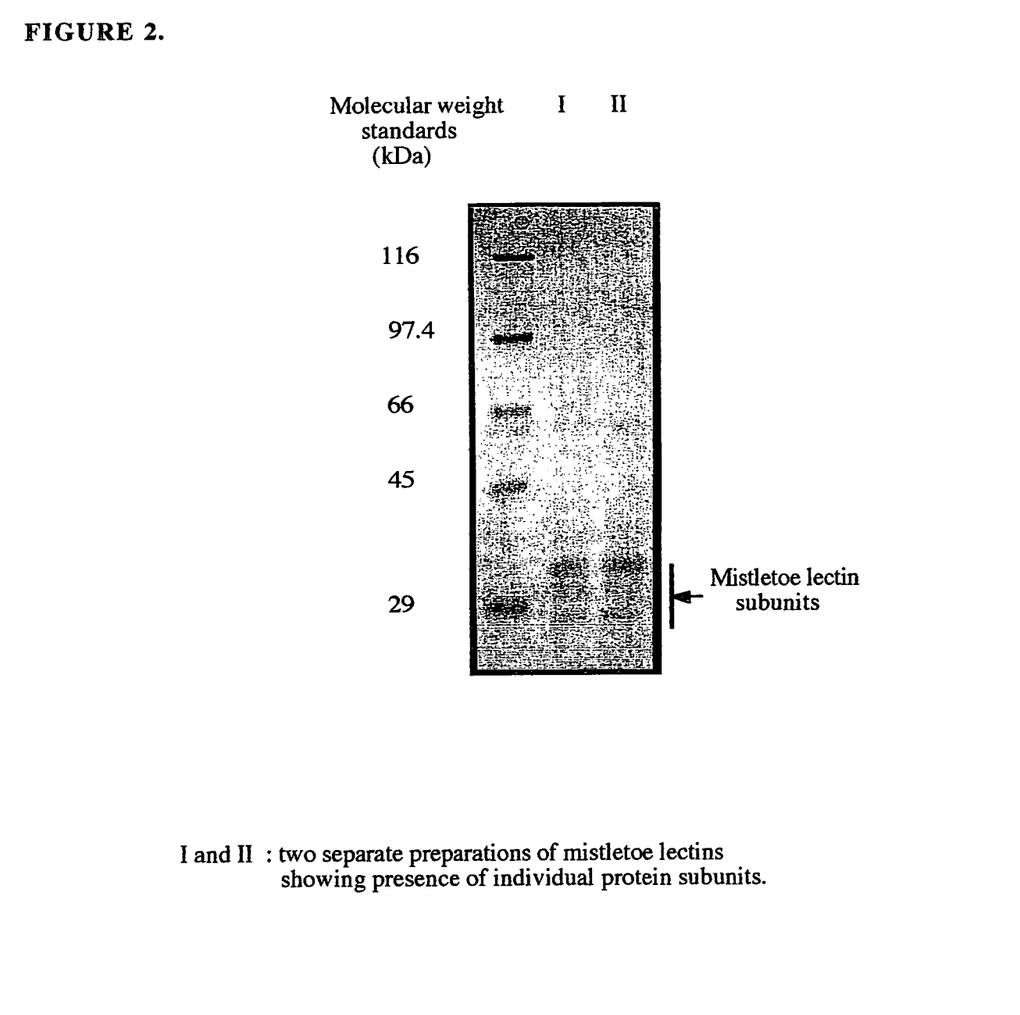
FIG. 2 is a gel electrophoresis of the mistletoe lectin preparation.

Characterization of the Mistletoe Lectin Preparation.
1) The protein content of the final dialysed product, measured according to the method of Bradford, was 250 μg/ml.
2) The absorbance of 1 ml of the final dialyzed product at 280 nm was >3.
3) Proteins present in the preparation were monitored by performing SDS polyacrylamide gel electrophoresis, as shown in FIG. 2. The major bands coincided with proteins within the range 29-35 kDa as expected for the subunits of the mistletoe lectins.
4) Biological activity confirmed using a cytotoxic assay where the ability of ML's to prevent growth of freshly seeded CHO cells was tested.
5) The stability of the preparation according to the invention was checked over a five-week period. The preparation proved to be stable at 4 degrees C., room temperature, minus 20 degrees C. and minus 80 degrees C. It can be frozen and thawed rapidly at least five times without affecting its biological activity. When heated at 70 degrees C. or above for a minimum of five minutes, however, then 100% biological activity is lost. This illustrates that the traditional manner of using boiling water to make mistletoe tea renders the mistletoe lectins biologically useless.

Method of Use

According to one aspect of the invention, therapeutically effective doses of the mistletoe lectin preparation are administered orally to individuals suffering from cancer or other diseases, such as autoimmune diseases in order to induce an immunomodulating response. In a preferred embodiment, the preparation is administered in conjunction with a daily regimen of oral arginine.

According to another aspect of the invention, the mistletoe lectin preparation is administered in such a way as to provide direct contact between the preparation and tumor cells, in order to induce a direct cytotoxic response.

Determining Dosage: Biological Response to the Preparation in Human Volunteers: Antibodies to ML's.

It has been shown that when purified ML-1 was presented orally to rats then antibodies could at later times be detected in the blood (Lavelle et al. Immunology 2000, 99, 30-37), incorporated by reference herein.

Figure 3:
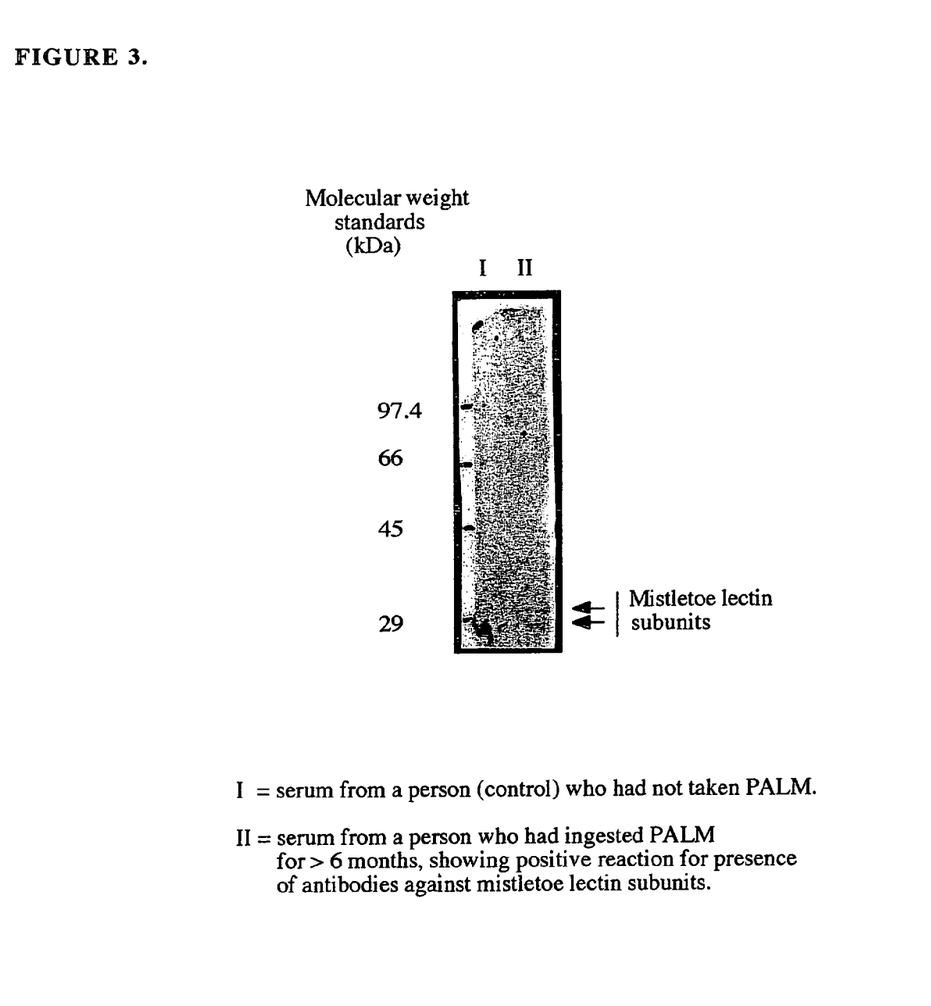
FIG. 3 is a gel electrophoresis of blood samples from a patient and a control.

This has now been adapted, according to the present invention, to test human individuals in order to determine whether or not a biological response to mistletoe lectins has been elicited following the oral intake of the enriched mistletoe preparation. Immunoblotting is performed using blood serum as a potential source of antibodies. As can be seen in FIG. 3 the serum from subject A is negative while that of subject B is positive. Subject B had taken the preparation orally for several months while subject A (B's husband) had not. This procedure is thus used to monitor subjects, such that the appropriate dosage of the preparation could be determined i.e. the provision orally of sufficient lectin to promote an antibody response.

The dosage originally administered was 1 ml taken 3 times per week, on a Monday-Wednesday-Friday regime, for a period of up to six weeks. The dosages are taken on alternating days in order to permit de-saturation of the receptors of the small intestine. It has been observed in the case of tumors of the large intestine, where direct contact between the preparation and the tumor itself is also desirable, that the dosage may need to be increased in order to first saturate the receptors in the small intestine, so that the lectins are able to reach the tumor site.

The following doses have now shown to provide the best clinical effect:

The preparation according to the invention, provided in 1 ml ampules, is mixed (for ease of consumption) in 2 dl water or another cold beverage, and taken three times per week as follows: Mondays 1 ml; Wednesdays 2 ml and Fridays 1 ml. Arginine is taken every day in the mornings and evenings.

The appropriate dosage of arginine is dependent on body weight. In the preferred embodiment, a dosage of between 0.001 and 0.01 g of arginine per kg of body weight is used. For ease of consumption, the arginine is mixed with 2 dl water or other beverage.

Examples from Human Volunteers.

To date over 150 patients with different types of cancer have been enrolled in a single-patient survey. No selection criteria have been applied. Patients include those with cancer in the digestive system, nervous system, different forms of gynecological cancer and skin cancer in terminal stages.

The patients have either been treated by staff of oncological departments without any offer of further treatment, or have been in terminal stages of hospital treatment. All patients have been in a poor state of health. It was desirable to investigate whether or not oral lectins could be offered as a positive form of treatment for this patient group.

Periodic blood samples have been taken and different forms of examination have been carried out (CT, X-ray, ultrasound). Therapeutic consultation with the patients providing necessary information has been central in the treatment.

Summary of experience hitherto with this form of treatment:

- A. For about 10% of the patients, decreased tumor size (both primary and secondary tumors) has been observed. Confirmed by CT, X-ray, ultrasound.
- B. About 25% of the patients have shown stagnation of tumor growth with a reduction of secondary phenomena such as fluid in the peritoneal cavity, swelling around the tumor etc.
- C. Another 30% have shown an arrest of tumor growth with stabilization of their condition.
- D. In a further 30% of patients a much slower progression of tumor growth has been experienced than that expected without the treatment.
- E. Approximately 5% of the patients have not shown any response.

In initial trials in human volunteers, several individuals have experienced clear signs of β-endorphin production. This is reflected in that 100% of the patients have reported a feeling of pleasant "warmness" and in general note a better general condition (sense of "ease"). In addition improved digestive function has been reported and a major decrease in pain level has been experienced.

There has been a clear indication that patients taking the preparation have had a higher level of tolerance during chemotherapy and/or radiotherapy than those not receiving the preparation.

Hitherto there have been no reports of any form of side-effects.

The preparation has in addition been used in the treatment of a limited number of patients suffering from auto-immune disease such as rheumatic disorders. The treatment has proved to have a marked effect by reducing joint swelling and decreasing the pain level, with a general improvement in the quality-of-life. The general effect on patients with rheumatic disorders is similar to that experienced with cancer patients who are under treatment.

Individual Cases

The following are several indicative examples of specific observations:

- A. One (bedridden) individual suffering from terminal prostate cancer with metastasis to the basal spine was given by his doctor in November 1998 a survival time of a matter of weeks. Within 2 months of oral intake of the preparation according to the invention his health had improved so drastically that he was able to attend his son's 50th birthday celebrations.
- B. A 23 year female with intense abdominal pain, was diagnosed as suffering from stomach cancer. She was scheduled for surgery in order to remove her stomach. Began treatment with the mistletoe lectin preparation. Within 5 days she noted considerably less pain. Ten days later (4 days prior to operation) she was subjected to gastroscopy. The stomach tumor (the size of a plum) was considerably reduced in size and the operation postponed. Two months later a new gastroscopy showed no signs of the tumor and she was declared symptom free. This was almost certainly due to the direct cytoxic effect of the preparation on the tumor cells.
- C. 55 year old male, operated in 1972 with a Bilroth II gastrectomy due to ulcer. 2000 detected adenocarcinoma of ventriculus with metastases to the peritoneum. Inoperable. Treated with palliative chemotherapy. No response to treatment, bad prognosis. Treatment with preparation according to the invention, later combined with arginine, stabilized health status. After one year of treatment, CT of abdomen showed virtual absence of ascites, no metastases and no original tumor. Clinically this patient is free of detectable cancer.
- D. 49 year old female with ovarian cancer with metastasis to the lymph system and peritoneum. Inoperable. Clinically adenocarcinoma. Started treatment with preparation immediately. Three weeks later at staging procedure, in which a biopsy was to be performed, no tumor or metastasis was detectable. As a result, no chemotherapy or radiation treatment was deemed necessary. Clinical improvement to near normal health. This patient has been treated with the preparation and arginine alone.
- E. 55 year old female diagnosed with breast cancer in 1998. Treated with operation, radiation and hormone therapy, yet still developed metastasis to lung and skeleton. After six weeks treatment with the preparation and arginine, x-ray and ultrasound scans showed decreased tumor and metastasis size. Clinically more energy and no pain. Discontinued use of painkillers.
- F. 34 year old female. Cancer of the ovary six years prior, developed metastasis to the pelvis. Began treatment with the mistletoe preparation. At staging procedure three weeks later, the tumor was significantly reduced in size. Began treatment with radiation, chemotherapy and hypothermia, concomitant with treatment with the preparation. Results: no detectable tumor or metastasis.

Mechanisms of Action

The observed patient data are consistent with the following properties of orally presented mistletoe lectins (ML), which are "negative" for tumor growth:

- I) Stimulation of intestinal hyperplasia which induces a competition for nutritional factors between tumor and intestine.
- II) Stimulation of lymphocyte infiltration into the tumor.
- III) Local release of cytokines from macrophages and lymphocytes (e.g. tumor necrosis factor alpha) into the tumor. These are detrimental to the tumor and reduce growth.
- IV) NKC (natural killer cells) activated and these "attack" the tumor cells.
- V) Apoptosis ("natural cell death") occurs in the tumor cells as a result of II), III) and IV).
- VI) Anti-angiogenic response, which results in a marked reduction in the number of blood capillaries in the tumor. Together with I) nutrient supply to the tumor reduced.

VII) If the tumor is "exposed" (e.g. stomach, colon) then ML may exert its cytotoxic effects i.e. uptake of ML by the tumor cells results in cell death through inhibition of protein synthesis.

Pharmaceutical Preparation

While it is possible for the mistletoe lectin preparation according to the invention to be utilized for therapy as a raw chemical composition, it may be advantageous to present the mistletoe lectins in the form of a pharmaceutical preparation.

A further aspect of the invention is therefore a pharmaceutical preparation comprising the mistletoe lectin preparation, or a pharmaceutically acceptable salt or derivative thereof, together with one or more pharmaceutically acceptable carriers and possibly other therapeutic or prophylactic ingredients. Said carriers must be acceptable, in that they are compatible with the other ingredients in the preparation and pose no risk to the patient.

Pharmaceutical preparations include those that are adapted for oral, rectal, nasal, topical, or vaginal administration, as well as inhalation and bladder infusion.

The mistletoe lectin preparation, together with conventional additives, carriers or diluting agents, can be used to prepare pharmaceutical compositions, including individual doses thereof, in the form of tablets, filled capsules, or fluids such as solutions, mixtures, emulsions, elixirs or capsules filled with such, all for oral intake, as well as in the form of suppositories for rectal administration. Such pharmaceutical compositions and individual doses thereof can comprise conventional ingredients or principles, and such dosage-forms can contain any effective concentration of the active ingredients in accordance with the intended daily dosage range. Preparations that contain approximately 0.25 mg of the mistletoe lectin preparation per individual dosage unit are representative of an appropriate concentration.

The pharmaceutical preparation according to the invention can be administered in a wide range of dosage-forms. Carriers used to produce a pharmaceutical preparation containing the mistletoe lectin preparation can include both solid and liquid substances. Solid dosage-forms may include powders, tablets, pills, capsules, suppositories, or dispersible granules. A solid carrier can be one or more substances that function as a diluting agent, flavor additive, solvent, lubricant, suspension agent, binder, preservative, tablet-disintegrating substance or encapsulating material.

In powdered form, the carrier is a finely pulverized solid including lactose, hydroxypropylmethylcellulose and PVP, mixed with an appropriate amount of finely pulverized mistletoe lectin preparation.

Appropriate carriers for powder and tablet forms include magnesium carbonate, magnesium stearate, talc, sugar, lactose, pectin, dextrin, stiffeners, gelatins, tragacanth, methylcellulose, and sodium carboxymethylcellulose. The term "preparation" is meant to include dosage-forms where the active ingredients are enclosed in an encapsulating material whether or nor associated with a carrier, including capsules or lozenges.

Suppositories are produced by melting a low-melting point wax and distributing the mistletoe lectin preparation therein. The melted, homogeneous mixture is then poured into forms and allowed to cool.

Preparations appropriate for vaginal administration can be presented as presses, tampons, creams, gels, pastes, foams or sprays that include, in addition to the active ingredient, suitable carriers known in the art.

Preparations in liquid form include solutions, suspensions, and emulsions, for example aqueous or propylene glycol solutions, together with coloring agents, flavor additives, stabilizing agents or diluting agents as appropriate. Also included are preparations in solid form that are meant to be converted to liquid form shortly prior to consumption. These forms may include, in addition to the active ingredients, artificial colors, flavors, stabilizers, buffers, natural or artificial sweeteners, dispersing agents, thickeners, dissolving agents and the like.

For topical administration to the epidermis, the mistletoe lectin preparation can be presented in the form of salves, creams, gels, skin washes or transdermal plasters. Salves and creams can be formulated with an aqueous or oil base, with the addition of suitable thickeners and/or gels. Skin washes can be prepared with an aqueous or oil base and may contain one or more emulsifying agents, stabilizers, dispersing agents, thickeners or fragrances.

Preparations suitable for topical administration in the mouth include lozenges that comprise active ingredients in an inert, flavored base, such as sucrose and arabica gum, as well as mouth washes containing the active ingredients in a liquid carrier.

Solutions or mixtures may be administered directly to the nasal cavity using conventional means, such as drops or sprays. The preparation may be produced in individual or multi-dose forms. Multi-dose forms would include a dropper, pipette or atomizer that delivers a predetermined volume of the preparation.

Administration to the respiratory tract may be achieved by the use of an aerosol preparation in which the active ingredients are placed in a pressurized container together with a suitable delivery agent, such as CFC, trichlorofluormethane, dichlorofluormethane, carbon dioxide or other suitable gas. The dosage may be controlled by an appropriate valve-system.

The pharmaceutical preparation is preferably provided in individual dosage units that contain a suitable amount of the active ingredients. The individual doses may be provided in a package, or possibly as a kit that includes a measuring device.

*All publications and articles identified below are specifically incorporated by reference into the preceding specification*

REFERENCES

1. The plant lectins PHA and ML-1 suppress the growth of a lymphosarcoma tumour in mice. I. F. Pryme, S. Bardocz, G. Grant, S. W. B. Ewen, A. Pusztai & U. Pfüller COST 98 vol. 5 (1998), 215-220.
2. The effects of PHA and mistletoe lectin binding to epithelium of rat and mouse gut. S. W. B. Ewen, S. Bardocz, G. Grant, I. F. Pryme & A. Pusztai COST 98 vol. 5 (1998), 221-225.
3. Does oral ingestion of ML-1 lectin ablate murine transplanted non-Hodgkin lymphoma by apoptosis or necrosis?S. W. B. Ewen, I. F. Pryme, S. Bardocz & A. Pusztai COST 98 vol. 6 (1999) 126-133.
4. A diet containing the lectin phytohaemagglutinin (PHA) slows down the proliferation of Krebs II ascites cell tumours in mice. I. F. Pryme, A. Pusztai & S. Bardocz Cancer Lett. 76 (1994) 133-137.
5. Phytohaemagglutinin in the diet induces growth of the gut and modifies some organ weights in mice. S. Bardocz, G. Grant, T. J. Duguid, D. S. Brown, M. Sakhri, A. Pusztai, I. F. Pryme, D. Mayer & K. Wayβ Med. Sci. Res. 22 (1994) 101-103.

6. The initial growth rate of Krebs II ascites cell tumours in mice is slowed down by the inclusion of phytohaemagglutinin in the diet. I. F. Pryme, A. Pusztai & S. Bardocz Int. J. Oncol. 5 (1994)1105-1107.
7. Effect of phytohaemagglutinin on the growth of Krebs II tumour cells, body metabolism and internal organs of mice. S. Bardocz, G. Grant, T. J. Duguid, D. S. Brown, A. Pusztai & I. F. Pryme Int. J. Oncol. 5 (1994) 1369-1374.
8. Switching between control and phytohaemagglutinin-containing diets affects growth of Krebs II ascites cells and produces differences in the levels of putrescine, spermidine and spermine. I. F. Pryme, S. Bardocz, G. Grant, T. J. Duguid, D. S. Brown & A. Pusztai. Cancer Lett. 93 (1995) 233-237.
9. Phytohaemagglutinin-induced gut hyperplasia and the growth of a mouse lymphosarcoma tumor. I. F. Pryme, A. Pusztai, G. Grant & S. Bardocz J. Exptl. Therap. & Oncol. 1 (1996) 171-176.
10. The effect of switching between PHA-containing and a control diet on the growth and lipid content of a Krebs II lymphosarcoma tumour. I. F. Pryme, A. Pusztai, G. Grant & S. Bardocz J. Exptl. Therap. & Oncol. 1 (1996) 273-277.
11. Dietary phytohaemagglutinin slows down the proliferation of a mouse plasma (MPC-11) tumour in Balb/c mice. I. F. Pryme, A. Pusztai, G. Grant & S. Bardocz Cancer Lett. 103 (1996) 151-155.
12. Reduced growth of a MPC-11 tumour in mice fed a diet containing the plant lectin PHA. I. F. Pryme, A. Pusztai, G. Grant & S. Bardocz COST 98, 4 (1997) 120-125.
13. Inclusion of the plant lectin PHA in the diet and its effect on development of murine tumours. I. F. Pryme, S. Bardocz, G. Grant, T. J. Duguid, D. S. Brown & A Pusztai In: Effects of antinutrients on the nutritional value of legume diets. COST 98, 1 (1996) 34-40.
14. The plant lectin PHA as a tool for reducing the progression of tumour growth. I. F. Pryme, S. Bardocz, G. Grant, T. J. Duguid, D. S. Brown & A. Pusztai COST 98, 2 (1996) 24-29.
15. The effect of delaying the inclusion of the plant lectin PHA in the diet on the growth of a subcutaneous Krebs II tumour. I. F. Pryme, S. Bardocz, G. Grant, T. J. Duguid & A. Pusztai COST 98, 3 (1996) 86-90.
16. Intracellular levels of polyamines in Krebs II lymphosarcoma cells in mice fed phytohaemagglutinin-containing diets are coupled with altered tumour growth. S. Bardocz, G. Grant, T. J. Duguid, D. S. Brown, A. Pusztai & I. F. Pryme Cancer Lett. 121 (1997) 25-29.
17. Limiting the availability of polyamines for a developing tumour: An alternative approach to reducing tumour growth. I. F. Pryme, G. Grant, A. Pusztai & S. Bardocz In "Polyamines in Health and Nutrition" eds. S. Bardocz and A. White, pp. 283-291 (1999). Kluwer Academic Publishers, Norwell, Mass. USA.
18. The induction of gut hyperplasia and limitation of tumour growth by PHA in the diet. I. F. Pryme, A. Pusztai, S. Bardocz & S. W. B. Ewen Histology and Histopathology 13 (1998) 575-583.
19. A combination of dietary protein depletion and PHA-induced gut growth reduce the mass of a murine non-Hodgkin lymphoma I. F. Pryme, A. Pusztai, S. Bardocz & S. W. B. Ewen Cancer Lett. 139 (1999) 145-152.
20. Delayed feeding of phytohaemagglutinin after injection of Krebs II cells is successful in reducing tumour growth. I. F. Pryme, S. Bardocz, G. Grant & A. Pusztai COST 98, 6 (1999) 120-125.
21. Timing of feeding NMRI mice a phytohaemagglutinin-containing diet and effec on the growth of a Krebs II lymphosarcoma tumour. I. F. Pryme, A. Pusztai, G. Grant & S. Bardocz COST 98, 7 (1999) 91-95.
22. The growth of an established murine non-Hodgkin lymphoma tumour is limited by switching to a phytohaemagglutinin-containing diet. I. F. Pryme, A. Pusztai, S. Bardocz & S. W. B. Ewen Cancer Lett. 146 (1999) 87-91.
23. The extent of PHA-induced gut hyperplasia is reduced by a developing murine non-Hodgkin tumour. I. F. Pryme, S. Bardocz, A. Pusztai & S. W. B. Ewen COST 98, 8 (2000) 65-69.
24. Reduction in growth of a non-Hodgkin lymphoma tumour in mice fed a polyamine-poor phytohaemagglutinin-containing diet is reversed by addition of polyamines. I. F. Pryme, A. Pusztai, S. W. B. Ewen & S. Bardocz COST 917, 4 (2000)167-172.
25. Dietary mistletoe lectin supplementation and reduced growth of a murine non-Hodgkin lymphoma. I. F. Pryme, S. Bardocz, A. Pusztai and S. W. B. Ewen Histol. & Histopathol. In Press.
26. Effects of an orally administered mistletoe (type-2RIP) lectin on growth, body composition, small Intestinal structure, and insulin levels In young rats. A. Pusztai, G. Grant, E. Gelencser. S. W. B. Ewen, U. Pfuller, R. Eifler and S. Bardocz. J. Nutr. Biochem. 9 (1998) 31-36.

The invention claimed is:

1. A method to produce an orally ingestible composition of matter consisting essentially of mistletoe lectin I (ML-I), mistletoe lectin II (ML-II), and mistletoe lectin III (ML-III) essentially without nausea inducing compounds, the method comprising the following steps:
   i) pulverizing a start material consisting of pieces of Viscum album,
   ii) mixing the pulverized material with three to ten times the amount of 0.2 M acetic acid on w/w basis to form a solution and stirring said solution 12 to 24 hours at temperatures between 1 and 8° C.,
   iii) filtering the solution through a coarse cloth, followed by filtering through a paper filter to remove turbidity and obtain a crude extract,
   iv) performing cationic exchange chromatography of the crude extract from (iii) on a cationic exchanger,
   v) washing the cationic exchanger with 0.15 M acetate buffer (pH 4.0) until absorption at 280 nm <0.5,
   vi) eluting ML-I, ML-II and ML-III collectively using a buffer containing 0.1 M Tris-HCl (pH 8.0) and 0.5 M NaCl and collecting fractions,
   vii) pooling fractions with absorbance >1.0 at 280 nm and dialyzing the pooled fractions overnight against 10 volumes of PBS (minus NaCl) to obtain a final extract,
   viii) aliquoting the final extract.

2. Method according to claim 1, wherein the solution in step ii) contains five times the amount of 0.2M acetic acid on a w/w basis and is stirred 12 hours, wherein in step (iv) 5 g of cationic exchanger is used to 1.0 liter of crude extract, and that the pooled fractions in step vii) are dialysed using a membrane having a cutoff size of MW 10,000.

3. Method according to claim 2, wherein the aliquots in step viii) are 1 ml.

4. Method for treating a patient suffering from cancer comprising rally administering to said patient the composition produced by the method of claim 1, in suitable doses to elicit a biological response, said response being selected from the group consisting of:
   a. an immune response
   b. stimulation of intestinal hyperplasia
   c. induction of cytokine production
   d. activation of Natural Killer Cells e. induction of an anti-angiogenic effect in a tumor, and
f. exertion of a direct cytotoxic effect on a tumor,
   wherein the composition is administered together with a supplemental substance for augmenting the effect of the preparation, and that said supplemental substance is arginine.

5. Method according to claim 4, wherein arginine is administered at a dose of between 0.001 and 0.01 g of arginine per kg of body weight every morning and evening.

6. A kit comprising an airtight package containing the composition produced by the method of claim 1, together with devices for metering oral dosages, wherein the kit further comprises arginine.

* * * * *